(12) United States Patent
Hunt

(10) Patent No.: US 6,882,414 B2
(45) Date of Patent: Apr. 19, 2005

(54) BROADBAND INFRARED SPECTRAL SURFACE SPECTROSCOPY

(75) Inventor: Jeffrey H. Hunt, Chatsworth, CA (US)

(73) Assignee: The Boeing Company, Chicago, IL (US)

( * ) Notice: Subject to any disclaimer, the term of this patent is extended or adjusted under 35 U.S.C. 154(b) by 392 days.

(21) Appl. No.: 10/174,874

(22) Filed: Jun. 19, 2002

(65) Prior Publication Data

US 2003/0234925 A1 Dec. 25, 2003

(51) Int. Cl.⁷ .............................................. G01N 21/88
(52) U.S. Cl. .............................. 356/237.2; 356/239.7; 250/559.41
(58) Field of Search ................ 356/237.1, 237.2–237.5, 356/239.1–239.8, 600, 317–334; 250/559.4–559.49

(56) References Cited

U.S. PATENT DOCUMENTS

| | | | | |
|---|---|---|---|---|
| 4,807,991 A | * | 2/1989 | Carew | 356/72 |
| 5,294,289 A | | 3/1994 | Heinz et al. | |
| 5,530,544 A | * | 6/1996 | Trebino et al. | 356/450 |
| 5,623,341 A | * | 4/1997 | Hunt | 356/300 |
| 5,875,029 A | | 2/1999 | Jann et al. | |
| 5,883,714 A | | 3/1999 | Jann et al. | |
| 5,898,499 A | | 4/1999 | Pressesky | |
| 5,923,423 A | | 7/1999 | Sawatari et al. | |
| 5,973,778 A | * | 10/1999 | Hunt | 356/300 |
| 6,141,100 A | * | 10/2000 | Burka et al. | 356/451 |
| 6,317,514 B1 | | 11/2001 | Reinhorn et al. | |
| 6,359,451 B1 | | 3/2002 | Wallmark | |

OTHER PUBLICATIONS

"Light Waves at the Boundary of Nonlinear Media"—The Physical Review, 128, p. 193, 1962, Bloembergen and P.S. Pershan.

"Surface Studies by Optical Second Harmonic Generation: an Overview"—Journal of Vacuum Science and Technology B, vol. 3, No. 5, Sep. Oct. 1985, pp. 1464–1466, Y.R. Shen.

* cited by examiner

Primary Examiner—Richard A. Rosenberger
Assistant Examiner—Vincent P. Barth
(74) Attorney, Agent, or Firm—Shimokaji & Associates, P.C.

(57) ABSTRACT

The system has a single pulse spectrum capability for sensing the presence of contamination on a surface to be interrogated. The system includes a narrow frequency bandwidth visible pulse and broadband infrared pulse that are directed to the surface. An output wavelength discriminator receives the reflected sum-frequency that is generated. The output wavelength discriminator is substantially non-transmissive at the frequencies of the visible pulse and the infrared pulse, but is substantially transmissive at the sum-frequency of the visible pulse and the infrared pulse. The output of the wavelength discriminator is a broadband output. A frequency disperser receives the output of the wavelength discriminator and provides a physical separation of output wavelengths of the broadband output. A multi-channel analyzer analyzes the intensity of the physically separated output wavelengths as a function of their physical positions. Thus, a wavelength dependent intensity measurement is provided that is indicative of the presence of contamination.

26 Claims, 1 Drawing Sheet

BROADBAND INFRARED SPECTRAL SURFACE SPECTROSCOPY

BACKGROUND OF THE INVENTION

1. Field of the Invention

The present invention relates to surface spectroscopy and more particularly to the use of second-order nonlinear optics to provide a means to rapidly generate wavelength dependent intensity measurements indicative of the physical spectroscopic properties of a surface, including the presence of contamination.

2. Description of the Related Art

In nonlinear optics, outputs are produced at sum, difference or harmonic frequencies of the input(s). Using second order nonlinear optical surface spectroscopy to examine the physical properties and behavior of a surface or interface was originally proposed in the 1960's, in "Light Waves at the Boundary of Nonlinear Media" by Bloembergen and P. S. Pershan, The Physical Review, 128, Page 193 (1962). Experimental work involving second harmonic generation was also performed. However, because lasers at the time were comparatively feeble, impractical, slow, etc., there was little subsequent work done on the development of second harmonic generation or, more generally, second order nonlinear optical (NLO) processes at surfaces until considerably later.

Recently, researchers have reviewed NLO processing and concluded that lasers had developed enough that they could be used for studying the physical and chemical properties of surfaces and interfaces. For example, a theoretical study of the physics of the interface, and not its engineering aspects, has been performed. See Journal of Vacuum Science and Technology B, Volume 3, Number 5, September October 1985, Pages 1464–1466, Y. R. Shen, "Surface Studies by Optical Second Harmonic Generation: an Overview."

In U.S. Pat. No. 5,294,289, T. F. Heinz et al. discuss the use of second harmonic generation as a means to monitor the epitaxial growth of silicon semiconductor structures in a high vacuum chamber. Specifically, they examined the spectroscopic response at the interface between the electronically active silicon and the insulative layer of calcium fluoride. By monitoring the magnitude of the resonance, they could ascertain whether the insulator was present on the surface and whether it had electronically binded to the underlying semiconductor. The system that is used examines only the use of second harmonic generation. As such, it only monitors the spectroscopic response one wavelength at a time. This is because the system, as described, uses a narrow-band spectroscopic source as its input. In order to generate a spectrum, the input has to be tuned to a series of input wavelengths. It also only applies to semiconductor growth and there is no discussion of the detection of contamination.

In U.S. Pat. No. 5,623,341, J. H. Hunt discusses the use of sum-frequency generation for the detection of contamination and corrosion on engine parts. In this incarnation, one of the inputs is a tunable IR beam that is tuned to a resonance of the contamination on the surface. The efficiency of the sum-frequency process is increased (so-called resonant enhancement) when the IR beam is resonant with a contaminant. If the contaminant is not present, there is no resonant enhancement. By comparing on and off resonant signals, the presence and level of contaminant can be deduced. However, this patent specifically discusses only narrowband single-frequency inputs.

In U.S. Pat. No. 5,875,029, P. C. Jann et al. describe a versatile optical inspection instrument and method to inspect magnetic disk surfaces for surface defects. The device provides surface position information of the defects. However, the technique involves only linear optical processes. That is, the input and output light wavelengths are the same. There is also no discussion of contamination monitoring.

In U.S. Pat. No. 5,883,714, Jann et al. describe a versatile optical inspection instrument and method to inspect magnetic disk surfaces for surface defects. The device is based on interferometric measurement and detects contaminants by measuring the Doppler shift in the light that results from scanning the light onto a contaminant or defect. By scanning, the device provides surface position information of the defects. However, the technique involves only linear optical processes and senses only phase changes. That is, the input and output light wavelengths are the same and there is no discussion of contamination measurement.

In U.S. Pat. No. 5,898,499, J. L. Pressesky discusses a system for detecting local surface discontinuities in magnetic storage discs. The device is an interferometric detector which scans the disc in a spiral motion. Local defects cause local changes in phase which are measured by interferometric techniques. This is a linear optical technique.

In U.S. Pat. No. 5,932,423, T. Sawatari et al. discuss a scatterometer for detecting surface defects in semiconductor wafers. This device is a linear interferometric device.

In U.S. Pat. No. 5,973,778, J. H. Hunt discusses the use of second harmonic changes in the second harmonic polarization to determine surface molecular alignment. There is no discussion of broadband infrared spectroscopic measurements in this patent.

In U.S. Pat. No. 6,317,514 B1, S. Reinhom et al. discuss a method and apparatus for inspecting a wafer surface to detect the presence of conductive material on the wafer. The device uses UV initiated electron emission to determine the location of conductive areas. Those areas which are metal will emit electrons. If the area, which is supposed to be conductive, is not, there will be no electron emission.

In U.S. Pat. No. 6,359,451 B1, G. N. Wallmark discusses a system for testing for opens and shorts between conductor traces on a circuit board. The technique uses electron scattering to perform its diagnostics and has no optics associated with it.

SUMMARY

The present invention is a surface contamination analyzing system with single pulse spectrum capability for sensing the presence of contamination on a surface to be interrogated. The system includes a first optical source for providing a narrow frequency bandwidth visible pulse directable to a location on a surface to be interrogated. A second optical source provides a broadband infrared pulse that covers substantially the entire infrared response of contamination that may be present on the surface. The broadband infrared pulse is directable to the surface to be interrogated. The infrared pulse and the visible pulse are alignable so that their surface locations of optical illumination overlap on the interrogated location. An output wavelength discriminator receives the reflected sum-frequency generated on the interrogated location. The output wavelength discriminator is substantially non-transmissive at the frequencies of the visible pulse and the infrared pulse, but is substantially transmissive at the sum-frequency of the visible pulse and the infrared pulse. The output of the output wavelength discriminator is a broadband output. A frequency disperser receives the broadband output of the output wavelength discriminator and provides a physical separation of output wavelengths of the broadband output. A multi-channel analyzer receives the physically separated output wavelengths of the frequency disperser and analyzes the intensity of the physically separated output wavelengths as a function of their physical positions. Thus, a wavelength dependent intensity measurement is provided that is indicative of the presence of contamination.

The characterization of surface conditions, especially at low levels of surface contamination, has a great deal of significance for many technical applications. As is evident from the historical study of physical chemistry, resonant spectral responses in the infrared provide the most exact information detailing of the materials being examined. This is because excitations at those wavelengths correspond to vibrational excitations in molecules, which are easy to classify and associate with specific internal molecular motions. In the present incarnation, the use of second order nonlinear optics makes the process surface specific, so that small changes in surface properties lead to a large change in the optical signal. If infrared spectroscopic features need to be examined, one of the inputs will be a tunable IR source. Since high peak powers are generally necessary to perform nonlinear optical measurements, the IR source will typically be an optical parametric oscillator designed to operate in the infrared. Heretofore, in this field, the infrared source has been operated at a narrow bandwidth, so that the infrared input has been tuned and the spectrum was slowly created. Using a broadband infrared input produces a broadband sum-frequency output containing all the features associated with the infrared response. At that point, the spectrum can be analyzed. Since the spectrum is generated all at once, the data acquisition speed in increased.

Other objects, advantages, and novel features will become apparent from the following detailed description of the invention when considered in conjunction with the accompanying drawings.

DETAILED DESCRIPTION OF THE INVENTION

Figure 1:
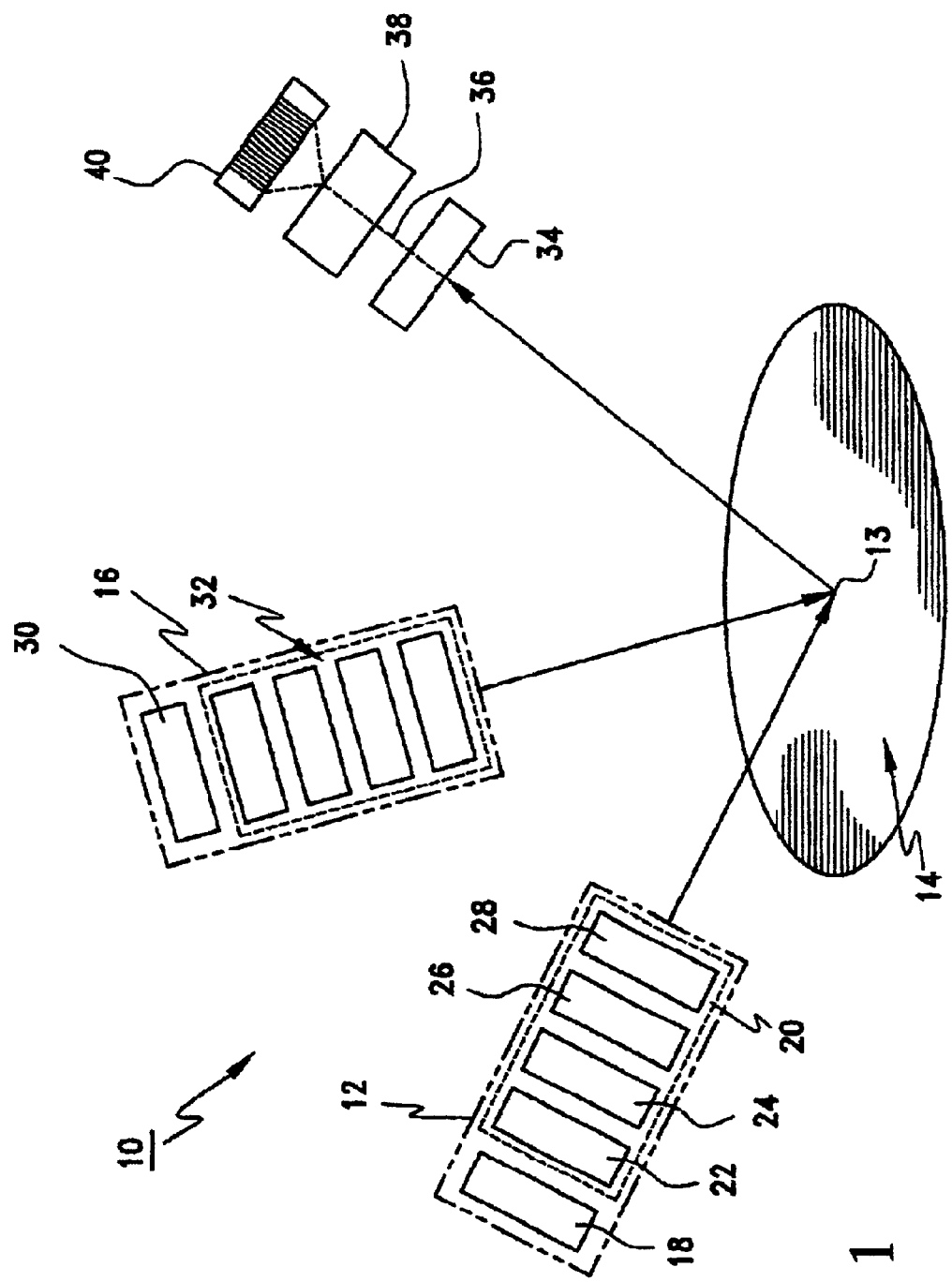
FIG. 1 is a schematic representation of the nonlinear optical system of the present invention.

Referring now to the drawings and the characters of reference marked thereon, FIG. 1 illustrates a preferred embodiment of the nonlinear optical system of the present invention, designated generally as 10. Diagnostic system 10 includes a first optical source, indicated by phantom lines 12 for providing a narrow frequency bandwidth visible pulse that is directable to a location 13 on a surface 14 of the semiconductor wafer to be interrogated. A second optical source 16 provides a broadband infrared pulse that is also directable to the location 13 on the surface 14 to be interrogated. The optical sources 12, 16 are aligned so that their surface areas of optical illumination overlap on the interrogated surface 14. This alignment may be implemented via a series of refractive and reflective elements. For example, by changing their tilt in two axes, two mirrors in series can propagate a laser beam to any position on a surface.

The first optical source 12 includes a narrow frequency bandwidth visible pulse input 18 in optical communication with an associated input optics 20. The input 18 is preferably a narrow frequency bandwidth visible pulse laser and may be, for example, a pulsed diode laser, a continuous wave diode laser, a pulsed solid state laser or continuous wave solid state laser. In certain applications, the laser wavelength may be fixed and in others it may be tunable.

The input optics 20 preferably includes an input polarizer 22, an input wavelength discriminator 24, an input spatial filter 26 and an input propagation optics 28. The input polarizer 22 could be, for example, a brewster angle polarizer, a thin film polarizer, a Glan-air or Glan-Thompson polarizer or other crystal polarizer. The wavelength discriminator 24 may be, for example, a color filter, a dielectric film, a holographic transmission filter or a grating. The input propagation optics 20 could be formed of one or more refractive or reflective optics which, when used in combination, control the divergence or convergence of the beam as it propagates towards the surface.

The second optical source 16 includes a broadband infrared pulse input 30 and associated input optics 32. The input optics 32 may be as described above with respect to the first optical source 12. However, the optics 32 is optimized for the wavelength of the second optical source 16. The input 30 is preferably a broadband infrared pulse laser and may be, for example, an optical parametric oscillator optimized for outputs in the infrared for a band between about 1.5 and 10 micron. The oscillator optics for generating the infrared will be designed to maximize the bandwidth output, so that substantially all of the infrared region of interest will be covered by that bandwidth. This can be accomplished by several means, such as using a pump laser for the parametric oscillator which has a wide bandwidth and using optics in the parametric oscillator which provide high reflectivity over a large regime. The broadband source infrared pulse should cover substantially the entire infrared response of contamination that may be present on the surface 14.

An output wavelength discriminator 34 receives the reflected sum-frequency generated on the interrogated location 13. The output wavelength discriminator 34 is substantially non-transmissive at the frequencies of the visible pulse and the infrared pulse, but is substantially transmissive at the sum-frequency of the visible pulse and the infrared pulse. The output 36 of said output wavelength discriminator is a broadband output. The output wavelength discriminator 34, like the input discriminator, may comprise a color filter, a dielectric film, a holographic transmission filter or a grating. Since the bandwidth of the infrared input is large, the bandwidth of the sum-frequency will be large. The output wavelength discriminator will have a correspondingly large bandwidth over which it is substantially transmissive.

A frequency disperser 38 receives the broadband output 36 of the output wavelength discriminator and provides a physical separation of output wavelengths of the broadband output. The frequency disperser 38 is preferably a prism. Alternatively, it may be a diffraction grating, since both prisms and gratings produce physical separations in the propagation direction of different output wavelengths.

A multi-channel analyzer 40 receives the physically separated output wavelengths of the frequency disperser 38 and analyzes the intensity of the physically separated output wavelengths as a function of their physical positions. Thus, a wavelength dependent intensity measurement is provided that is indicative of the presence of contamination. The multi-channel analyzer 40 may comprise, for example, a semiconductor linear array, which contains a pixelized semiconductor so that light received within a given pixel creates an electronic signal associated only with the light at that position.

In a preferred embodiment the first optical source may comprise a Nd:YAG laser operating on the 1.064 micron line or a Nd:YAG laser and a harmonic converter for operation at the second or third harmonic of the laser fundamental output wavelength. It may operate with a maximum pulse length of 10 nanoseconds. The optimal pulse length is less than 1 picosecond.

The input optics of the first optical source preferably includes a steering apparatus, comprising two mirrors aligned so that that their surface normals are non-coplanar. It also preferably includes a polarization rotator comprising a half-wave plate. The half-wave plate should be optimized for an output wavelength of the input laser. The input optics also preferably uses a linear polarizer that is aligned so that an output wavelength is p or s polarized with the polarization referenced to the surface to be interrogated. A spot shaping apparatus is used, comprising a series of lenses, for creating a controlled spot size on the surface to be interrogated. Finally, a narrow band optical filter is used that passes only an output wavelength or harmonic wavelength of the input laser.

In this preferred embodiment, the second optical source preferably comprises a tunable IR input—an optical parametric oscillator and amplifier tunable output in a band of 1.5–10 microns. The oscillator optics will be configured so that the infrared output will contain a broadband bandwidth, covering all the infrared wavelengths of interest. A steering apparatus is utilized including two mirrors aligned so that their surface normals are non-coplanar, with the mirrors' reflectances being optimized for an output wavelength of the infrared laser. A polarization rotator is used that is operative in the infrared range. A linear polarizer is used and is aligned so that an output wavelength is p or s polarized with the polarization referenced to the surface to be interrogated. Again, a spot shaping apparatus is used, including a series of lenses for creating a controlled spot size on the surface to be interrogated, the lenses being transparent in the infrared range. Finally, an optical filter is utilized including a semiconductor crystal having a bandgap that passes infrared but blocks shorter wavelengths.

The output wavelength discriminator preferably includes an iris; a filter in optical communication with the iris for passing the sum frequency wavelength; and, a linear polarizer in optical communication with the filter, aligned to detect either the p or s polarized sum-frequency wavelength, wherein the polarization is referenced to the surface where the sum-frequency light is generated.

The frequency dispersive optics preferably includes a prism having coatings optimized for the sum frequency. The multi-channel analyzer preferably comprises a semiconductor linear array, including a silicon detector being electronically gated to only detect output light generated by the input laser pulses. A computer collects and analyzes the electronic data from the position sensitive detector.

Obviously, many modifications and variations of the present invention are possible in light of the above teachings. It is, therefore, to be understood that within the scope of the appended claims, the invention may be practiced otherwise than as specifically described.

What is claimed and desired to be secured by Letters Patent of the United States is:

1. A surface contamination analyzing system with single pulse spectrum capability for sensing the presence of contamination on a surface to be interrogated, comprising:
    a) a first optical source for providing a narrow frequency bandwidth visible pulse directable to a location on a surface to be interrogated;
    b) a second optical source comprising a broadband infrared pulse laser comprising an optical parametric oscillator for providing a broadband infrared pulse that covers substantially the entire infrared response of contamination that may be present on said surface, said broadband infrared pulse being directable to said surface to be interrogated, said infrared pulse and said visible pulse being alignable so that their surface locations of optical illumination overlap on said interrogated location;
    c) an output wavelength discriminator for receiving the reflected sum-frequency generated on said interrogated location, said output wavelength discriminator being substantially non-transmissive at the frequencies of said visible pulse and said infrared pulse, but being substantially transmissive at the sum-frequency of said visible pulse and said infrared pulse, the output of said output wavelength discriminator being a broadband output;
    d) a frequency disperser for receiving said broadband output of said output wavelength discriminator and providing a physical separation of output wavelengths of said broadband output; and,
    e) a multi-channel analyzer for receiving the physically separated output wavelengths of said frequency disperser and analyzing the intensity of said physically separated output wavelengths as a function of their physical positions, thus providing a wavelength dependent intensity measurement indicative of the presence of contamination.

2. The surface contamination analyzing system of claim 1, wherein said frequency disperser comprises a prism.

3. The surface contamination analyzing system of claim 1, wherein said frequency disperser comprises a diffraction grating.

4. The surface contamination analyzing system of claim 1, wherein said first optical source comprises a first laser in optical communication with a first input optics.

5. The surface contamination analyzing system of claim 1, wherein said first optical source comprises a first laser in optical communication with a first input optics, said first input optics comprising a first input polarizer, a first input wavelength discriminator, a first input spatial filter and first input propagation optics in optical communication.

6. The surface contamination analyzing system of claim 1, wherein said second optical source comprises a second laser in optical communication with a second input optics.

7. The surface contamination analyzing system of claim 1, wherein said second optical source comprises a second laser in optical communication with a second input optics, said second input optics comprising a second input polarizer, a second input wavelength discriminator, a second input spatial filter and second input propagation optics in optical communication.

8. The surface contamination analyzing system of claim 1, wherein said first optical source comprises a pulsed solid state laser.

9. The surface contamination analyzing system of claim 1, wherein said first optical source comprises a Nd:YAG laser operating on the 1.064 micron line.

10. The surface contamination analyzing system of claim 1, wherein said first optical source comprises a Nd:YAG laser and a harmonic converter for operation at the second or third harmonic of the laser fundamental output wavelength.

11. The surface contamination analyzing system of claim 1, wherein said first optical source comprises a Nd:YAG laser operating on the 1.064 micron line and a maximum pulse length of 10 nanoseconds.

12. The surface contamination analyzing system of claim 1, wherein said first optical source comprises a Nd:YAG laser operating on the 1.064 micron line and a pulse length of less than 1 picosecond.

13. The surface contamination analyzing system of claim 1, wherein said second optical source comprises a broadband infrared pulse laser.

14. The surface contamination analyzing system of claim 1, wherein said second optical source comprises a broadband infrared pulse laser, comprising an optical parametric oscillator optimized for outputs in the infrared for a band between about 1.5 and 10 micron.

15. The surface contamination analyzing system of claim 1, wherein said multi-channel analyzer comprises a semiconductor linear array.

16. The surface contamination analyzing system of claim 1, wherein said multi-channel analyzer comprises a semiconductor linear array including a pixelized semi-conductor.

17. A method for sensing the presence of contamination on a surface to be interrogated, comprising the steps of:

a) directing a narrow frequency bandwidth visible pulse to a location on a surface to be interrogated;

b) directing a broadband infrared pulse laser, comprising an optical parametric oscillator optimized for outputs in the infrared for a band between about 1.5 and 10 micron, that covers substantially the entire infrared response of contamination that may be present on said surface, comprises a broadband infrared pulse laser, comprising an optical parametric oscillator optimized for outputs in the infrared for a band between about 1.5 and 10 micron, said broadband infrared pulse being directed to said surface to be interrogated, said infrared pulse and said visible pulse being aligned so that their surface locations of optical illumination overlap on said interrogated location;

c) receiving the reflected sum-frequency generated on said interrogated location, via an output wavelength discriminator, said output wavelength discriminator being substantially non-transmissive at the frequencies of said visible pulse and said infrared pulse, but being substantially transmissive at the sum-frequency of said visible pulse and said infrared pulse, the output of said output wavelength discriminator being a broadband output;

d) receiving said broadband output of said output wavelength discriminator and providing a physical separation of output wavelengths of said broadband output; and, e) receiving the physically separated output wavelengths of said frequency disperser and analyzing the intensity of said physically separated output wavelengths as a function of their physical positions, thus providing a wavelength dependent intensity measurement indicative of the presence of contamination.

18. The method of claim 17, wherein said step of providing a physical separation of output wavelengths of said broadband output comprises utilizing a prism.

19. The method of claim 17, wherein said step of providing a physical separation of output wavelengths of said broadband output comprises utilizing a diffraction grating.

20. The method of claim 17, wherein said step of directing a narrow frequency bandwidth visible pulse comprises directing a laser.

21. The method of claim 17, wherein said step of directing a narrow frequency bandwidth visible pulse comprises directing a pulsed diode laser.

22. The method of claim 17, wherein said step of directing a first laser input comprises directing a Nd:YAG laser operating on the 1.064 micron line.

23. The method of claim 17, wherein said step of directing narrow frequency bandwidth visible pulse comprises directing a Nd:YAG laser operating on the 1.064 micron line and a maximum pulse length of 10 nanoseconds.

24. The method of claim 17, wherein said step of directing a narrow frequency bandwidth visible pulse comprises directing a Nd:YAG laser operating on the 1.064 micron line and a pulse length of less than 1 picosecond.

25. The method of claim 17, wherein said step of directing a narrow frequency bandwidth visible pulse comprises directing a pulsed diode laser.

26. A surface contamination analyzing system with single pulse spectrum capability for sensing the presence of contamination on a surface to be interrogated, comprising:

a) a first optical source for providing a narrow frequency bandwidth visible laser pulse directable to a location on a surface to be interrogated, said first optical source being a Nd:YAG laser;

b) a second optical source for providing a broadband infrared laser pulse, comprising an optical parametric oscillator optimized for outputs in the infrared for a band between about 1.5 and 10 micron, that covers substantially the entire infrared response of contamination that may be present on said surface, said broadband infrared pulse being directable to said surface to be interrogated, said infrared pulse and said visible pulse being alignable so that their surface locations of optical illumination overlap on said interrogated location:

c) an output wavelength discriminator for receiving the reflected sum-frequency generated on said interrogated location, said output wavelength discriminator being substantially non-transmissive at the frequencies of said visible pulse and said infrared pulse, but being substantially transmissive at the sum-frequency of said visible pulse and said infrared pulse, the output of said output wavelength discriminator being a broadband output;

d) a frequency disperser for receiving said broadband output of said output wavelength discriminator and providing a physical separation of output wavelengths of said broadband output; and, e) a multi-channel analyzer for receiving the physically separated output wavelengths of said frequency disperser and analyzing the intensity of said physically separated output wavelengths as a function of their physical positions, thus providing a wavelength dependent intensity measurement indicative of the presence of contamination.

* * * * *